(12) United States Patent
Sillender

(10) Patent No.: US 10,188,426 B2
(45) Date of Patent: Jan. 29, 2019

(54) EMBRYO TRANSFER CATHETER AND METHOD

(71) Applicant: Mark Sillender, Bicton (AU)

(72) Inventor: Mark Sillender, Bicton (AU)

( * ) Notice: Subject to any disclaimer, the term of this patent is extended or adjusted under 35 U.S.C. 154(b) by 593 days.

(21) Appl. No.: 14/760,351

(22) PCT Filed: Feb. 6, 2014

(86) PCT No.: PCT/AU2014/000091
§ 371 (c)(1),
(2) Date: Jul. 10, 2015

(87) PCT Pub. No.: WO2014/121333
PCT Pub. Date: Aug. 14, 2014

(65) Prior Publication Data
US 2015/0342642 A1 Dec. 3, 2015

(30) Foreign Application Priority Data
Feb. 6, 2013 (AU) ............................... 2013900396

(51) Int. Cl.
*A61M 25/00* (2006.01)
*A61B 17/435* (2006.01)
(Continued)

(52) U.S. Cl.
CPC ......... *A61B 17/435* (2013.01); *A61M 25/003* (2013.01); *A61M 25/0017* (2013.01);
(Continued)

(58) Field of Classification Search
CPC .... A61M 2210/1433; A61M 2210/145; A61B 17/425; A61B 17/43
See application file for complete search history.

(56) References Cited

U.S. PATENT DOCUMENTS

RE29,207 E * 5/1977 Bolduc .................. A61B 17/42
128/831
5,150,718 A 9/1992 De Nijs
(Continued)

FOREIGN PATENT DOCUMENTS

EP 0412664 A1 * 2/1991 ........ A61M 25/1011
WO 82/00754 3/1982
(Continued)

OTHER PUBLICATIONS

Meriano, James, et al., "The Choice of Embryo Transfer Catheter Affects Embryo Implantation After IVF," Oct. 2010, Elsevier Science Inc., vol. 74, No. 4, pp. 678-682.*
(Continued)

*Primary Examiner* — Thaddeus B Cox
(74) *Attorney, Agent, or Firm* — Hamre, Schumann, Mueller & Larson, P.C.

(57) ABSTRACT

An embryo transfer catheter (10) is described comprising an outer catheter body (12) having first and second lumens (14, 16). The second lumen (16) is adapted to receive an internal catheter (not shown) with a single lumen which, in use, will allow passage of an embryo or embryo-containing cannula (not shown) into the uterus (18) of the recipient. An inflatable balloon (20) is provided at a distal end of the first lumen (14). The inflatable balloon (20) is designed to be as small as possible in its inflated condition while still being retained in the uterus (18). The shape of the balloon (20) is adapted in its inflated state to conform to just the lowest part of the uterus (18). The aim in designing the balloon (20) as small as possible is to leave as much endometrium accessible to the embryo for implantation as possible, and to occupy as little volume as possible within the uterine cavity and to exert as little pressure as possible to avoid causing contractions, while still being retained in the uterus (18).

9 Claims, 4 Drawing Sheets

(51) Int. Cl.
*A61M 25/10* (2013.01)
*A61M 31/00* (2006.01)

(52) U.S. Cl.
CPC ......... *A61M 25/1002* (2013.01); *A61M 31/00* (2013.01); *A61M 2025/0039* (2013.01); *A61M 2202/0007* (2013.01); *A61M 2210/1433* (2013.01)

(56) References Cited

U.S. PATENT DOCUMENTS

| | | | |
|---|---|---|---|
| 5,383,873 A | | 1/1995 | Hoey et al. |
| 5,451,232 A | | 9/1995 | Rhinehart |
| 5,562,654 A | | 10/1996 | Smith |
| 5,613,950 A | | 3/1997 | Yoon |
| 5,904,665 A | | 5/1999 | Muharib |
| 6,010,448 A | * | 1/2000 | Thompson ............ A61B 17/43 600/114 |
| 6,050,935 A | * | 4/2000 | Ranoux ................ A61B 17/435 600/33 |
| 6,063,395 A | | 5/2000 | Markkula et al. |
| 6,476,079 B1 | | 11/2002 | Jukarainen et al. |
| 2002/0082635 A1 | * | 6/2002 | Kammerer ........ A61M 25/1002 606/193 |
| 2003/0229373 A1 | | 12/2003 | Lee |
| 2004/0247674 A1 | | 12/2004 | Haapakumpu |
| 2005/0021069 A1 | | 1/2005 | Feuer |
| 2006/0058831 A1 | | 3/2006 | Atad |
| 2008/0146873 A1 | * | 6/2008 | Adams ................ A61B 1/303 600/104 |
| 2009/0024108 A1 | * | 1/2009 | Lee-Sepsick .... A61B 17/12099 604/515 |
| 2009/0137970 A1 | * | 5/2009 | George ............. A61B 17/4241 604/271 |
| 2012/0143209 A1 | * | 6/2012 | Brecheen ............... A61B 17/42 606/119 |
| 2015/0359566 A1 | | 12/2015 | Sillender |

FOREIGN PATENT DOCUMENTS

| | | |
|---|---|---|
| WO | 95/32756 | 12/1995 |
| WO | 97/16217 | 5/1997 |
| WO | 01/21081 | 3/2001 |
| WO | 2012/013229 | 2/2012 |

OTHER PUBLICATIONS

Supplementary European Search Report issued in European Application, No. 14748819.1, dated Sep. 19, 2016, 5 pages.
Supplementary European Search Report issued in European Application, No. 14748804.3, dated Aug. 10, 2016, 9 pages.
Yanushpolsky, et al., "Transcervical placement of a Malecot catheter after hysteroscopic evaluation provides for easier entry into the endometrial cavity for women with histories of difficult intrauterine inseminations and/or embryo transfers: a prospective case series", Fertility and Sterility, vol. 73, No. 2, pp. 402-405, Feb. 2000.
Cook Medical, 2009 Product Catalog, Assisted Reproductive Technology, Part VI: Embryo Transfer, Sydney IVF Embryo transfer Catheter Sets—3 pages www.medial.cz/data/files/medial/download/katalogy/Cook/Cook_ivf_katalog.pdf.
Medical Device Kitazato et Catheters 3FR 22CM-213322, published Sep. 28, 2012, 2 pages http://www.medicaldevices24.com/medical_devices/info/kitazato-et-catheters-3fr-22crn/419702.
Office Action issued in European Patent Application No. 14748804.3, dated Apr. 26, 2018, 4 pages.

* cited by examiner

EMBRYO TRANSFER CATHETER AND METHOD

FIELD OF THE INVENTION

The present invention relates to a new embryo transfer catheter and relates particularly, though not exclusively, to such an embryo transfer catheter for use in an in-vitro fertilisation procedure. The invention also relates to an improved method of transferring embryos in an in-vitro fertilisation procedure.

BACKGROUND TO THE INVENTION

A common assisted reproduction technology, in-vitro fertilisation (IVF) and its derivatives, allows for the retrieval of male sperm & female oocytes by various methods. This is followed by immediate use or storage of these gametes. Fertilisation of the oocyte(s) under strictly controlled conditions occurs immediately or at a later date. Embryos formed by this process are grown in optimal surroundings for a variable time in the laboratory and assessed. The embryos are then replaced in the genital tract, most commonly the uterus, of the female where they will hopefully implant in the endometrium of the uterus, leading to an ongoing pregnancy.

There are many potential points of failure in this overall process. Success rates of IVF have increased slowly but gradually over time. An important step in the IVF process is the replacement of the embryo in the female, most commonly in the uterus. In this step, the clinician examines the female and exposes the uterine cervix with a speculum. The cervix is cleaned. A catheter is inserted through the cervix into the uterine cavity. International Patent Application No PCT/US00/26313 (Cook Urological Inc) describes a prior art embryo transfer catheter designed for this purpose. Ultrasound is often used to guide placement. This catheter may be stiff to enable more forceful passage through the cervix, which can be tortuous. Alternatively, the catheter can be soft to allow a passage that follows the anatomy without forcing. Some catheters have both hard and soft sections.

A further internal catheter is inserted through this outer catheter, and its distal end protrudes from the outer catheter as the outer catheter is possibly withdrawn slightly. The inner catheter is then positioned, optimally under ultrasound control, to a point near the fundus, or top, of the uterine cavity. Better results are obtained if this inner catheter is soft and passage is atraumatic. Finally, when correct placement has been judged, a further cannula containing embryos, culture fluid for nourishment, and sometimes air bubbles to aid ultrasound visualisation, is rapidly deployed through the inner catheter, flushed to eject the contents, and then withdrawn with checks to confirm the embryos have been ejected into the uterus. When this is confirmed, all catheters are withdrawn and the patient rests for a variable amount of time. An older technique uses only two catheters, and the inner catheter is used for both positioning and transfer of embryos.

There are several ways that success rates may vary that are attributable to this embryo transfer step in the assisted reproduction process:

1. Passage of the outer catheter though the cervix might be difficult. Manipulation or forceful passage of the catheter leads to irregular contractions in the uterus. When the embryos are inserted, these contractions can lead to the embryos ending in the Fallopian tubes where they may become ectopic pregnancies. Alternatively, contractions may lead to the embryos flushing out through the cervix once the transfer catheter is removed. There is research to show that the number and quality of irregular contractions is correlated with success or failure of embryo transfer. Also, there is research showing reduced success if there is blood and mucus, a sign of traumatic insertion, on the catheter once withdrawn.
2. There may be sub-clinical infection present at the cervix. There is research showing reduced pregnancy success when there is mucopurulent discharge visible at embryo transfer.
3. Following removal of the embryo transfer cannula, the embryos may be expelled from the uterus prior to their implantation. This may be the case even if transfer is easy. Varying periods of bed rest to reduce this chance have been tried with inconclusive results.
4. Even if the embryos remain in the uterus, there may be uterine conditions that prevent or reduce implantation. One reason is the total area of healthy endometrium available for implantation may be reduced by fibroids or a septum in the uterus. Another reason might be that the endometrium has not responded well to hormonal manipulation prior to transfer, and is less receptive. There may be subclinical infection in the cavity or endometrium, perhaps exacerbated by passage of the catheter through an infectious cervix.

Therefore, it could be postulated, embryo quality and other maternal factors being equal, that:

$$\text{Implantation rate} \propto \text{Area and quality of endometrium} * \text{Time in the cavity to allow implantation}$$

The present invention was developed with a view to providing a new embryo transfer catheter which may be left securely in situ before and after embryo transfer for several days or longer and which minimises physical disturbance of the endometrium at the time of embryo transfer, and inhibits expulsion of embryos. The invention also provides an improved method of transferring an embryo into the uterine cavity. Although the embryo transfer catheter and method will be described with particular reference to human use, it will be understood that the device and method may also be used with animals.

References to prior art in this specification are provided for illustrative purposes only and are not to be taken as an admission that such prior art is part of the common general knowledge in Australia or elsewhere.

SUMMARY OF THE INVENTION

According to one aspect of the present invention there is provided an embryo transfer catheter for transferring an embryo into a uterine cavity of a recipient, the catheter comprising:
an outer catheter body having first and second lumens, the second lumen being adapted to receive an internal catheter which, in use, will allow passage of an embryo-containing cannula or direct passage of an embryo or embryos;
an inflatable balloon provided at a distal end of the first lumen, the inflatable balloon being designed to be as small as possible in its inflated condition whilst still being retained in the uterus, the shape of the balloon being adapted in its inflated state to conform to just the lowest part of the uterus.

Preferably the balloon is shaped to conform to the lowest part of the uterus both transversely and in an anterior-posterior direction. Preferably the balloon is shaped in a concave way transversely on its superior aspect, which provides the volume necessary for catheter retention and conforms to the transverse uterine shape, but leaves as much endometrium accessible as possible. Preferably the balloon is convex in an anterior-posterior dimension on its superior aspect (to encourage movement of the embryo to the endometrium rather than allow it to rest centrally on the balloon), taking up minimal room in the smaller anterior-posterior dimension of the flattened uterine cavity, whilst still being retained in the uterus.

Typically the balloon comprises first and second arms, which in an inflated state extend upwards transversely within the uterus, at an angle approximating the slope of the inner transverse walls of the flattened uterine cavity.

Another possible variation helps retention of the balloon and hence the catheter. Optionally the balloon may be augmented by inferior protuberances providing extra resistance to expulsion of the catheter. These protuberances typically deflate and become flaccid when the balloon is deflated allowing atraumatic removal. Advantageously these protuberances also enhance the seal of the balloon, when inflated, to the lower part of the uterus, blocking embryo expulsion.

Preferably the portion of the outer catheter body located on the vaginal aspect of the cervix is secured by means of a locking plastic device or an inflatable balloon device for holding the correctly positioned catheter in place more securely following embryo transfer. Either one of these devices preferably slides up and down the outer catheter body prior to be being secured or inflated so it lies snugly adjacent to the external aspect of the cervix, securing it in a stable position without movement. This allows for good security, despite variation in the length of the cervix in different women. The locking device or sliding balloon device may have an additional flexible silicone or PVC cover, which envelops the distal end of the catheter, like a bag, preventing colonisation with infective organisms prior to the embryo transfer. This cover is then removed at the time of transfer.

The length of the catheter is such that it limits that portion of its length protruding into the vagina to enhance comfort. However, it still remains accessible in order to allow inflation of the balloon using the first lumen, or passage of catheters through the second lumen. Alternatively, the length of the vaginal portion of the catheter can be longer, even long enough to protrude through the vaginal introitus. This variation would allow easy subsequent embryo transfer without need for another speculum examination. Similarly, removal could then take place without speculum examination.

Advantageously the outer catheter body may be coated with a polymer or membrane, which allows the controlled release of therapeutic substances, locally to the cervix and uterus. Possibly useful therapeutic substances that could be utilised in embryo transfer include:

Aspirin (which would inhibit the uterine contractions previously discussed that prevent implantation).

Antibiotics (to treat prior infection or prevent organisms introduced during transfer causing infection, reducing implantation rates).

Hormones (to promote growth or receptivity of the endometrium and sustain the pregnancy e.g. oestradiol, oestriol, oestrone and other synthetic oestrogenic derivatives, progesterone and other synthetic progestogenic derivatives, growth hormone, growth hormone releasing hormone, DHEA and its isomers, analogues and derivatives, prostacyclin, alpha and beta human chorionic gonadotrophin, luteinising hormone etc.).

Corticosteroids, for instance prednisolone, methylprednisolone, hydrocortisone, cortisone, betamethasone, dexamethasone, fluocortolone, triamcinolone, budesonide, their derivatives, analogues, isomers and related class members (to reduce inflammation and promote implantation).

Sildenafil and other phosphodiesterase type 5 inhibitors, their derivatives and their analogues (to enhance endometrial receptivity promoting implantation).

Immunomodifiers, for example monoclonal antibodies designed to reduce the activity of inflammatory cells and substances, azathioprine, interferons, immunosuppressants like cyclosporin, tacrolimus, sirolimus and mycophenolate, and endometrial receptor agonists and antagonists.

Calcium channel blockers, for instance Dihydropyridine calcium channel blockers, including but not limited to nifedipine, amlodipine, nicardipine, nimodipine etc; Phenylalkylamine calcium channel blockers like verapamil; Benzothiazepine calcium channel blockers like diltiazem; and non-selective agents like mibefradil, bepridil, fluspirilene, and fendiline (to reduce contractions that diminish successful implantation).

Nitric oxide, nitroglycerine, isosorbide mononitrate, nitroprusside and other nitric acid donors, to reduce contractions and promote implantation.

Growth factors and cytokines (these are under research presently with ill-defined therapeutic effects and clinical indications).

Local anaesthetics (to reduce any discomfort from the catheter, and also reduce possible signalling within the uterus which may lead to contractions that reduce implantation). Examples are Benzocaine, Chloroprocaine, Cocaine, Cyclomethycaine, Dimethocaine/Larocaine, Piperocaine, Propoxycaine, Procaine/Novocaine, Proparacaine, Tetracaine/Amethocaine, Lidocaine, Articaine, Bupivacaine, Cinchocaine/Dibucaine, Etidocaine, Levobupivacaine, Lidocaine/Lignocaine, Mepivacaine, Prilocaine, Ropivacaine, Trimecaine.

According to another aspect of the present invention there is provided an improved method of transferring an embryo into the uterus of a recipient, the method comprising the steps of:

providing an outer catheter body having first and second lumens, the first lumen having an inflatable balloon provided at its distal end;

up to several minutes, hours, days or weeks or longer before the actual embryo transfer:
  inserting the outer catheter body into the uterus through the cervix;
  inflating the balloon with fluid so that the outer catheter body is retained in the uterus;
  closing off the second lumen to prevent infection and/or blockage, if embryo transfer is not immediate;

at the time of the embryo transfer:
  opening the second lumen in the outer catheter body;
  inserting a matching internal catheter into the second lumen;
  passing an embryo-containing cannula through the internal catheter to transfer an embryo into the uterus;
  or, alternatively, passing only one catheter, already containing embryos, through the second lumen and transferring the embryos directly;

following embryo transfer:
reclosing the second lumen; and,
retaining the outer catheter body in the uterus for up to several hours or days after the embryo transfer wherein, in use, the transferred embryo or embryos are prevented from expulsion by obstruction of the cervix and physical disturbance of the endometrium can be minimised.

Possibly the balloon may be temporarily partially deflated during the embryo transfer to allow adjacent passage of the internal soft catheter into the uterine cavity. If so, the balloon is reinflated immediately after embryo transfer and removal of the embryo-bearing cannula or catheter.

Typically the step of closing off the second lumen in the outer catheter body is performed by inserting a removable flexible plastic stent that is lockable in position by a locking mechanism. The locking mechanism may be a Luer-Lok (Trademark). Preferably the step of opening the second lumen is performed by removing the flexible stent. Typically the step of reclosing the second lumen is performed by inserting a new flexible stent in the second lumen to occlude it. Alternatively, the second lumen is closed by means of a self-closing lid at the distal aspect and a lid or cap at the proximal end.

Advantageously step of inserting the embryo transfer catheter through the cervix and into the uterine cavity includes placing a tight-fitting covering or sleeve received over the catheter to protect the catheter from contacting any cervical mucus or infection. Once the catheter has been inserted into the uterus, the sleeve is preferably removed by simply pulling it distally. Preferably the sleeve is split at the top allowing its removal so as to leave the catheter in place.

Advantageously the method further comprises the step of controlled release of therapeutic substances via the outer catheter, locally to the cervix and uterus.

Throughout the specification, unless the context requires otherwise, the word "comprise" or variations such as "comprises" or "comprising", will be understood to imply the inclusion of a stated integer or group of integers but not the exclusion of any other integer or group of integers. Likewise the word "preferably" or variations such as "preferred", will be understood to imply that a stated integer or group of integers is desirable but not essential to the working of the invention.

BRIEF DESCRIPTION OF THE DRAWINGS

The nature of the invention will be better understood from the following detailed description of several specific embodiments of an embryo transfer catheter and improved method of embryo transfer, given by way of example only, with reference to the accompanying drawings, in which.

DETAILED DESCRIPTION OF PREFERRED EMBODIMENTS

Figure 1:
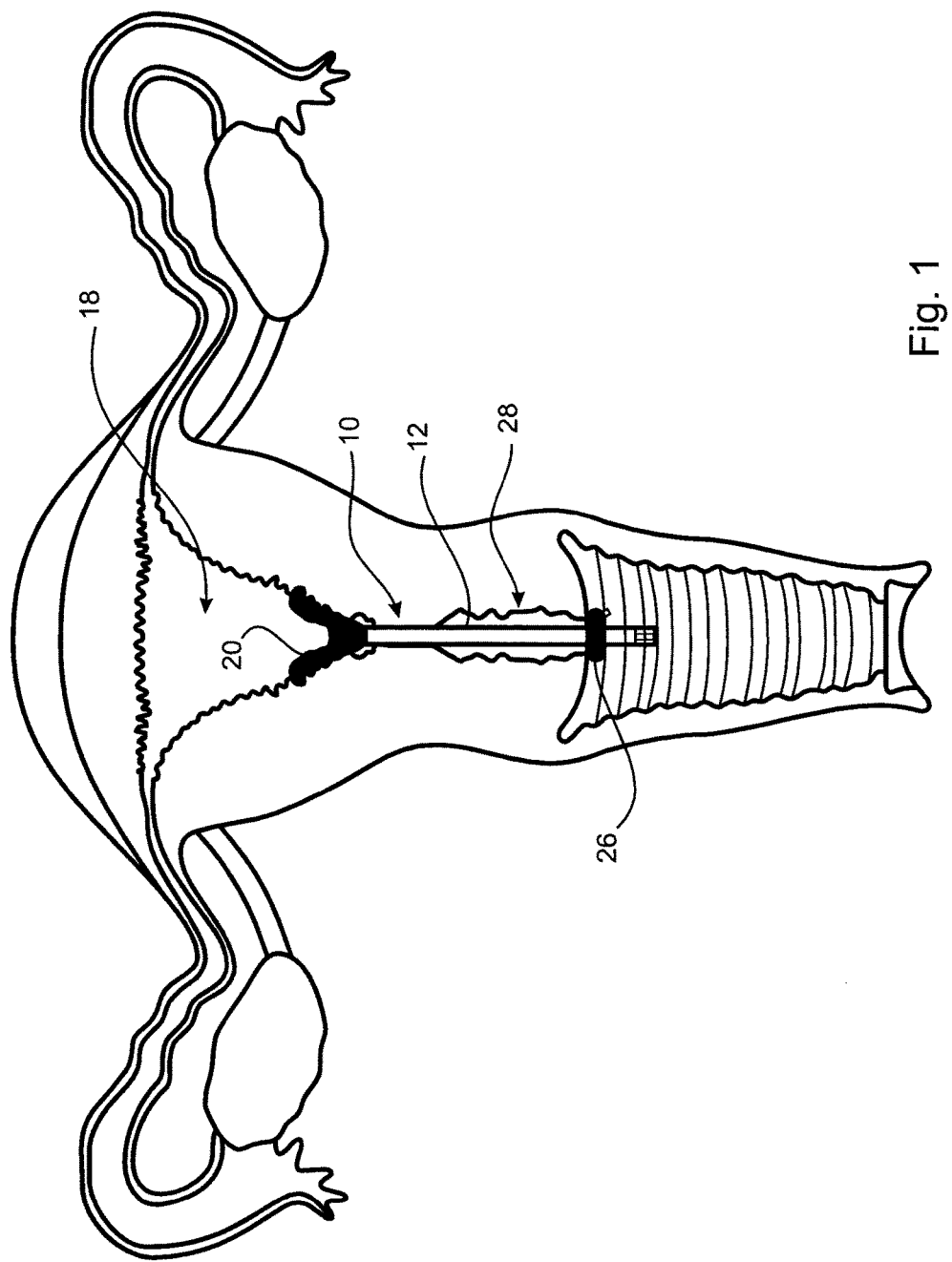
FIG. 1 illustrates a first embodiment of an embryo transfer catheter inserted into a uterus through the cervix of the recipient.
Figure 2:
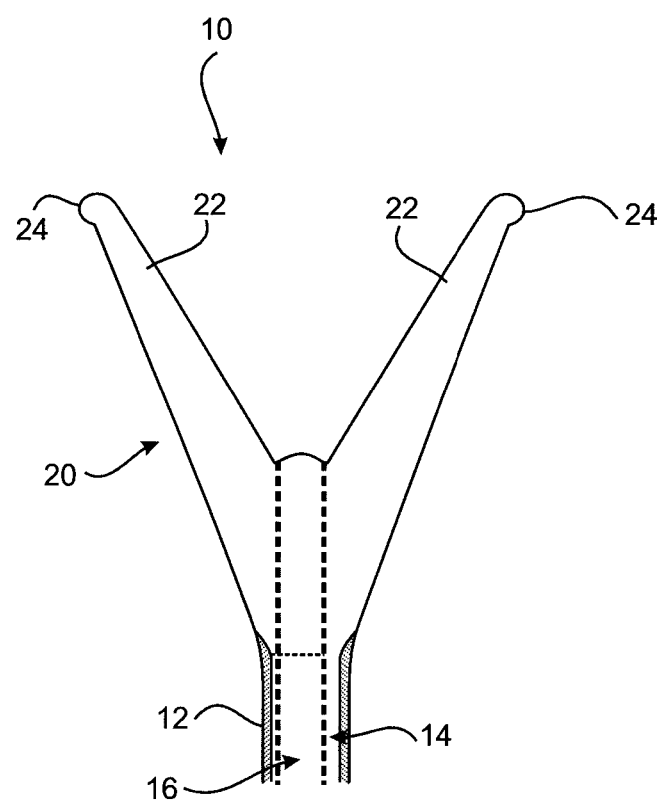
FIG. 2 illustrates the shape of a balloon on the distal end of the embryo transfer catheter of FIG. 1 in its inflated state.
Figure 3:
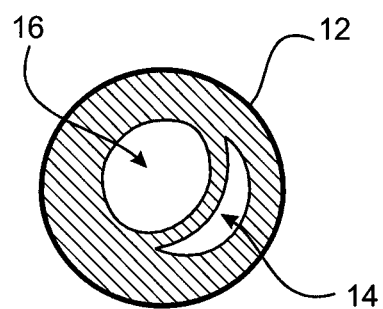
FIG. 3 is a cross-section view of the outer catheter body of the embryo transfer catheter of FIG. 1.

A first embodiment of an embryo transfer catheter 10 in accordance with the invention, as illustrated in FIGS. 1 to 3, comprises an outer catheter body 12 having first and second lumens 14, 16 (see FIG. 3), the second lumen 16 being adapted to receive an internal catheter (not shown) with a single lumen which, in use, will allow passage of an embryo or embryo-containing cannula (not shown) into the uterus 18 of the recipient. An inflatable balloon 20 is provided at a distal end of the first lumen 14. The inflatable balloon 20 is designed to be as small as possible in its inflated condition whilst still being retained in the uterus 18. The shape of the balloon 20 is adapted in its inflated state to conform to just the lowest part of the uterus 18.

Figure 5:
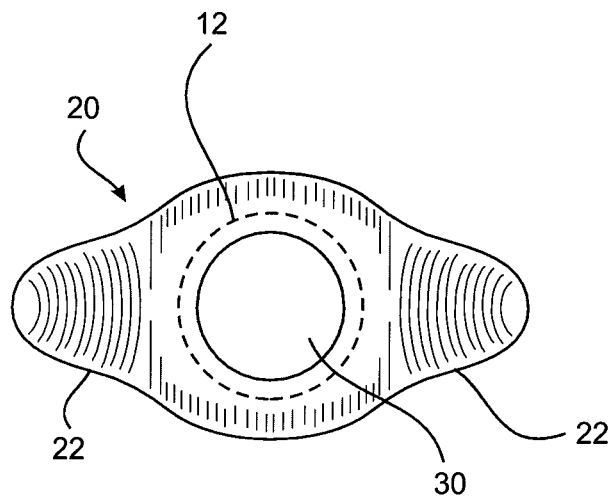
FIG. 5 is a top plan view of the embryo transfer catheter of FIG. 1 with the balloon in a semi-inflated state; and, FIG. 6 is a cross-section view of an alternative design for the outer catheter body of the embryo transfer catheter.

The aim in designing the balloon 20 as small as possible is to leave as much endometrium accessible to the embryo for implantation as possible, and to occupy as little volume as possible within the uterine cavity and to exert as little pressure as possible to avoid causing contractions, whilst still being retained in the uterus 18. FIG. 5 shows the profile of the balloon 20 when viewed in top plan view, in a semi-inflated state. In FIG. 5 the second lumen 16 is occluded by a stent 30 (or alternatively a lid).

Preferably the balloon 20 is shaped to conform to the lowest part of the uterus 18 both transversely and in an anterior-posterior direction. Preferably the balloon is shaped in a concave way transversely on its superior aspect, which provides the volume necessary for catheter retention and conforms to the transverse uterine shape, but leaves as much endometrium accessible as possible. Preferably the balloon is convex in an anterior-posterior dimension on its superior aspect (to encourage movement of the embryo to the endometrium rather than allow it to rest centrally on the balloon), taking up minimal room in the smaller anterior-posterior dimension of the flattened uterine cavity, whilst still being retained.

In the illustrated embodiment the balloon 20 comprises first and second arms 22, which in an inflated state extend upwards transversely within the uterus 18, at an angle approximating the slope of the inner transverse walls of the flattened uterine cavity.

Other possible variations help retention of the balloon 20 and hence the catheter: Optionally the balloon 20 may be augmented by inferior protuberances 24 providing extra resistance to expulsion of the catheter body 12. Several protuberances may be provided on each balloon to enhance tactile resistance to expulsion. These protuberances 24 typically deflate and become flaccid when the balloon 20 is deflated allowing atraumatic removal. Advantageously these protuberances 24 also enhance the seal of the balloon 20 to the lower part of the uterus 18, blocking embryo expulsion.

The use of protuberances on the balloon 20 is not the only way to secure the catheter within the uterus. For example, an assembly of two similarly shaped plastic arms with distal hinges could be deployed. The plastic arms would be straight (continuous with the catheter) upon insertion, but could then be pushed transversely, articulating via their hinges, at a chosen time by using the stent, pressing on a plastic protuberance. Then when removal occurs, the stent can be pulled out, allowing the plastic arms to fold back vertically facilitating catheter extraction.

Preferably the portion of the outer catheter body 12 on the vaginal aspect of the cervix is secured by means of a plastic locking device or an inflatable locking balloon device 26 for holding the correctly positioned catheter in place more securely following embryo transfer. Either one of these devices preferably slides up and down the outer catheter body 12 prior to be being secured or inflated, so that it lies snugly adjacent to the external aspect of the cervix 28, securing it in a stable position without movement, as shown in FIG. 1. This allows for secure retention of the catheter 10, despite variation in the length of the cervix in different women. The locking device or sliding balloon device may have an additional flexible silicone or PVC cover, which envelops the distal end of the catheter, like a bag, preventing colonisation with infective organisms prior to the embryo transfer. This cover is then removed at the time of transfer. The portion of the outer catheter body 12 on the vaginal aspect of the cervix can also be secured by simply using an increased friction technique. Current devices all use this simple friction technique.

The length of the catheter 10 is such that it limits that portion of its length protruding into the vagina to enhance comfort. However, it still remains accessible in order to allow inflation of the balloon 20 using the first lumen 14, or passage of catheters through the second lumen 16. Alternatively, the length of the vaginal portion of the catheter can be longer, even long enough to protrude through the vaginal introitus. This variation would allow easy subsequent embryo transfer without need for another speculum examination. Similarly, removal could then take place without speculum examination. This extra length would be advantageous when the catheter is only planned to be left for up to a few hours after embryo transfer.

A removable flexible plastic stent 30, that is lockable by a locking mechanism, typically a Luer-Lok (Trademark) or similar, is provided to close off the second lumen 16 prior to embryo insertion, to prevent infection and/or blockage. The top of the stent 30 would typically be gently convex to match the adjacent parts of the balloon 20. This stent 30 is removed for the embryo transfer, and subsequently replaced with a matching internal catheter with a single lumen, which then allows passage of the embryo or embryo-containing cannula.

Figure 6:
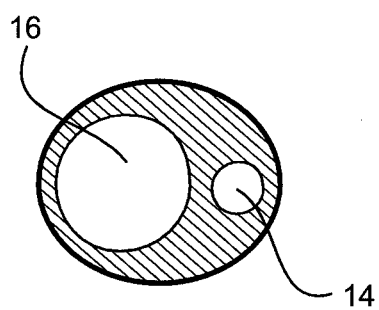

In FIG. 3 it can be seen how the cross-sectional shape of the first lumen 14 (for balloon inflation) of the outer catheter body 12 is crescent shaped. FIG. 6 illustrates an alternative cross-sectional design for the outer catheter body, in which the first lumen 14 is of circular shape.

Advantageously the outer catheter body 12 may be coated with a polymer or membrane, which allows the controlled release of therapeutic substances, locally to the cervix 28 and uterus 18. Possibly useful therapeutic substances that could be utilised in embryo transfer include:

Aspirin (which would inhibit the uterine contractions previously discussed that prevent implantation).

Antibiotics (to treat prior infection or prevent organisms introduced during transfer causing infection, reducing implantation rates).

Hormones (to promote growth or receptivity of the endometrium and sustain the pregnancy eg. oestradiol, oestriol, oestrone and other synthetic oestrogenic derivatives, progesterone and other synthetic progestin derivatives, growth hormone, growth hormone releasing hormone, DHEA and it's isomers, analogues and derivatives, prostacyclin, alpha and beta human chorionic gonadotrophin, luteinising hormone etc.)

Corticosteroids, for instance prednisolone, methylprednisolone, hydrocortisone, cortisone, betamethasone, dexamethasone, fluocortolone, triamcinolone, budesonide, their derivatives, analogues, isomers and related class members (to reduce inflammation and promote implantation).

Sildenafil and other phosphodiesterase type 5 inhibitors, their derivatives and their analogues (to enhance endometrial receptivity promoting implantation).

Immunomodifiers, for example monoclonal antibodies designed to reduce the activity of inflammatory cells and substances, azathioprine, interferons, immunosuppressants like cyclosporin, tacrolimus, sirolimus and mycophenolate, and endometrial receptor agonists and antagonists.

Calcium channel blockers, for instance Dihydropyridine calcium channel blockers, including but not limited to nifedipine, amlodipine, nicardipine, nimodipine etc; Phenylalkylamine calcium channel blockers like verapamil; Benzothiazepine calcium channel blockers like diltiazem; and non-selective agents like mibefradil, bepridil, fluspirilene, and fendiline (to reduce contractions that diminish successful implantation).

Nitric oxide, nitroglycerine, isosorbide mononitrate, nitroprusside and other nitric acid donors, to reduce contractions and promote implantation.

Growth factors and cytokines (these are under research presently with ill-defined therapeutic effects and clinical indications).

Local anaesthetics (to reduce any discomfort from the catheter, and also reduce possible signalling within the uterus which may lead to contractions that reduce implantation). Examples are Benzocaine, Chloroprocaine, Cocaine, Cyclomethycaine, Dimethocaine/Larocaine, Piperocaine, Propoxycaine, Procaine/Novocaine, Proparacaine, Tetracaine/Amethocaine, Lidocaine, Articaine, Bupivacaine, Cinchocaine/Dibucaine, Etidocaine, Levobupivacaine, Lidocaine/Lignocaine, Mepivacaine, Prilocaine, Ropivacaine, Trimecaine.

Figure 4:
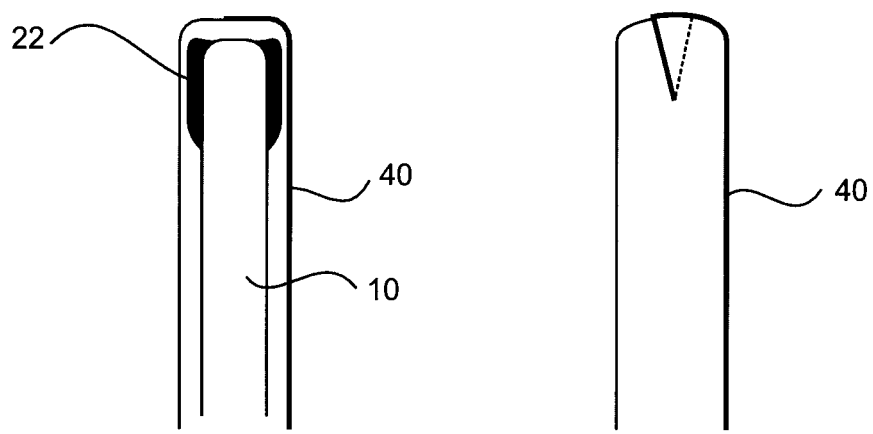
FIG. 4 illustrates a sleeve for insertion of the embryo transfer catheter of FIG. 1.

Advantageously the embryo transfer catheter 10 may be inserted through the cervix and into the uterine cavity within a tight-fitting covering or sleeve 40 (made of silicone or PVC or other non-embryo toxic flexible material), illustrated in FIG. 4. The sleeve 40 has a split at the top with overlapping portions. Once the catheter 10 has been inserted into the uterus, this silicone sleeve 40 is removed by simply pulling it distally, the split at the top allowing its removal leaving the catheter 10 in place. The sleeve 40 protects the catheter 10 from contacting any cervical mucus or infection. The sleeve 40 may be slightly textured or absorbent. This texture or absorbency encourages adherence of any cervical mucus brought into the uterus during the insertion, and thus allows the removal of this mucus when the sleeve 40 is removed.

A preferred method of transferring an embryo into the uterus 18 of a recipient will now be described with reference to FIG. 1. The method firstly comprises the step of providing an outer catheter body 12 having first and second lumens 14, 16, the first lumen having an inflatable balloon 20 provided at its distal end, as described above. The outer catheter body 12 may be inserted into the uterus 18 through the cervix 28 several hours or preferably several days or weeks or longer before the actual embryo transfer, instead of immediately prior as in current practice. Then the balloon 20 is inflated with fluid (liquid or gas) so that the outer catheter body 12 is retained in the uterus and cervix 18. The removable flexible plastic stent 30 is already placed to close off the second lumen 16 to prevent infection and/or blockage. Alternatively, the second lumen is closed by means of a lid at the distal aspect, and a lid or cap at the proximal end.

At the time of the embryo transfer the stent 30 is removed to open the second lumen in the outer catheter body for the embryo transfer. This stent is replaced with a matching internal catheter (not shown) with a single lumen, which then allows passage of the embryo, or alternatively an embryo-containing cannula to transfer an embryo into the uterus 18. The balloon 20 may be temporarily partially deflated during the embryo transfer to allow adjacent passage of the internal soft catheter into the uterine cavity. If so, it is reinflated immediately after embryo transfer and removal of the embryo-bearing cannula or catheter.

A new flexible stent 30 is placed in the second lumen 16 to occlude it following embryo transfer to reclose the second lumen 16. Alternatively, the distal lid closes following removal of the passed catheter and a cap or lid occludes the lumen on its proximal aspect. The outer catheter body 12 may be retained in the uterus 18 for up to several minutes, hours or days after the embryo transfer wherein, in use, physical disturbance of the endometrium can be minimised. The catheter's design allows it to be left securely in situ after embryo transfer for several days, which potentially increases success rates, by several methods, most importantly, by blockage of the exit of the uterus preventing expulsion of the embryo, and by further local delivery of therapeutic substances from the catheter body.

The possible advantages of prior insertion are:
- it allows for uterine contractions to settle if insertion is difficult
- it reduces the stress surrounding the embryo transfer
- it allows for timely insertion under anaesthetic if insertion failure occurs
- it allows local delivery of therapeutic substances over a period of time prior to embryo transfer (as described below).

Now that preferred embodiments of the embryo transfer catheter and method of embryo transfer have been described in detail, it will be apparent that the described embodiments provide a number of advantages over the prior art, including the following:

(i) Retention of the embryo transfer catheter pre-insertion allows for uterine contractions to settle if insertion is difficult.
(ii) It reduces the stress surrounding the embryo transfer.
(iii) It allows for timely insertion under anaesthetic if insertion failure occurs.
(iv) It allows local delivery of therapeutic substances over a period of time prior to embryo transfer.
(v) Retention of the embryo transfer catheter post-insertion ensures blockage of the exit of the uterus preventing expulsion of the embryo.
(vi) It maximizes contact of the embryo with the endometrium.
(vii) It also allows the local delivery of therapeutic substances over a period of time after embryo transfer which could enhance pregnancy rates by virtue of decreasing uterine contractions, reducing infection, immune response & inflammation, and delivery of hormones or growth factors.

It will be readily apparent to persons skilled in the relevant arts that various modifications and improvements may be made to the foregoing embodiments, in addition to those already described, without departing from the basic inventive concepts of the present invention. For example, the shape of the balloon at the distal end of the outer catheter body may vary significantly from that shown in the illustrated embodiments. The balloon may be of any suitable shape that leaves as much endometrium accessible to the embryo for implantation as possible, occupies as little volume as possible within the uterine cavity and exerts as little pressure as possible to avoid causing contractions, whilst still being retained in the uterus. Therefore, it will be appreciated that the scope of the invention is not limited to the specific embodiments described, and is to be determined from the appended claims.

The invention claimed is:

1. An improved method of transferring an embryo into a uterus via a cervix of a recipient, the method comprising:
    providing an outer catheter body having first and second lumens, the first lumen having an inflatable balloon provided at a distal end of the first lumen;
    up to several minutes, hours, days or weeks or longer before an embryo transfer:
        inserting the outer catheter body into the uterus through the cervix;
        inflating the balloon with fluid so that the outer catheter body is retained in the uterus;
        closing off the second lumen by inserting a removable flexible plastic stent that is closed and lockable in position by a locking mechanism;
    at the embryo transfer:
        opening the second lumen in the outer catheter body;
        inserting a matching internal catheter into the second lumen;
        passing an embryo or embryo-containing cannula through the internal catheter to transfer an embryo into the uterus;
    following embryo transfer:
        reclosing the second lumen; and,
        retaining the outer catheter body in the uterus for up to several hours or days or longer after the embryo transfer wherein, in use, the transferred embryo is prevented from expulsion by obstruction of the cervix and physical disturbance of an endometrium can be minimised.

2. An improved method of transferring an embryo as defined in claim 1, further comprising temporarily partially deflating the balloon during the embryo transfer to allow passage of an internal soft catheter into the uterus.

3. An improved method of transferring an embryo as defined in claim 2, further comprising after embryo transfer: removing the cannula or the internal soft catheter followed by reinflating the balloon.

4. An improved method of transferring an embryo as defined in claim 1, wherein opening the second lumen comprises removing the flexible plastic stent.

5. An improved method of transferring an embryo as defined in claim 4, wherein reclosing the second lumen comprises inserting a new flexible stent in the second lumen to occlude the second lumen.

6. An improved method of transferring an embryo as defined in claim 4, wherein reclosing the second lumen comprises using a self-closing lid at a distal aspect of the second lumen and a lid or cap at a proximal end of the second lumen.

7. An improved method of transferring an embryo as defined in claim 1, wherein inserting the outer catheter body through the cervix and into the uterus includes placing a tight-fitting covering or sleeve over the outer catheter body to protect the outer catheter body from contacting any cervical mucus or infection.

8. An improved method of transferring an embryo as defined in claim 7, further comprising removing the tight-fitting covering or sleeve once the outer catheter body has been inserted into the uterus by pulling the tight-fitting covering or sleeve proximally.

9. An improved method of transferring an embryo as defined in claim 1, wherein the method further comprises controllably releasing a therapeutic substance via the outer catheter body to the cervix and uterus.

\* \* \* \* \*